United States Patent [19]

Doyle

[11] 4,348,541
[45] Sep. 7, 1982

[54] METHANOL HOMOLOGATION USING COBALT-RUTHENIUM CATALYSTS

[75] Inventor: Gerald Doyle, Bridgewater, N.J.

[73] Assignee: Exxon Research and Engineering Company, Florham Park, N.J.

[21] Appl. No.: 98,981

[22] Filed: Nov. 30, 1979

[51] Int. Cl.³ .............. C07C 47/06; C07C 29/00; C07C 27/00; C07C 45/49
[52] U.S. Cl. .................. 568/487; 568/902; 568/890
[58] Field of Search ............ 260/601 R; 568/902, 568/890, 487

[56] References Cited

U.S. PATENT DOCUMENTS

| | | | |
|---|---|---|---|
| 3,248,432 | 4/1966 | Riley | 568/902 |
| 3,285,948 | 11/1966 | Butter | 260/601 R |
| 3,356,734 | 12/1967 | Kuraishi et al. | 260/601 R |
| 4,111,837 | 9/1978 | Taylor | 568/902 |
| 4,133,966 | 1/1979 | Pretzer et al. | 568/902 |
| 4,151,208 | 4/1979 | Pretzer et al. | 260/601 R |
| 4,171,461 | 10/1979 | Bartish | 568/902 |
| 4,239,924 | 12/1980 | Pretzer et al. | 568/902 |
| 4,253,987 | 3/1981 | Eluto | 568/902 |

FOREIGN PATENT DOCUMENTS

| | | |
|---|---|---|
| 13464 | 7/1980 | European Pat. Off. . |
| 22735 | 1/1981 | European Pat. Off. . |
| 220388 | 1/1981 | European Pat. Off. . |
| 2007652A | 5/1979 | United Kingdom . |

Primary Examiner—Werren B. Lone
Attorney, Agent, or Firm—James H. Takemoto

[57] ABSTRACT

Methanol can be selectively converted to acetaldehyde, ethanol or mixtures thereof, using a homogeneous process. The process comprises contacting methanol with carbon monoxide and hydrogen in the presence of a catalytic system containing cobalt-ruthenium complexes or a soluble ruthenium compound plus $Co_2(CO)_{8-n}$ where n is from 0 to 4.

16 Claims, 1 Drawing Figure

PRODUCT DISTRIBUTION VS. TIME

METHANOL HOMOLOGATION USING COBALT-RUTHENIUM CATALYSTS

BACKGROUND OF THE INVENTION

1. Field of the Invention

This invention relates to a homogeneous process for the homologation of methanol to acetaldehyde, ethanol or mixtures thereof. In one aspect of the invention, methanol is reacted with carbon monoxide and hydrogen in the presence of a catalytic system containing cobalt and ruthenium.

2. Description of the Prior Art

The production of ethanol from methanol, carbon monoxide and hydrogen in the presence of a cobalt catalyst and an iodine promoter and a ruthenium halide or osmium halide secondary promoter is disclosed in U.S. Pat. No. 3,285,948 (Butter). A similar catalyst system based on $Co_2(CO)_8$ is described by Metlin et al., Abstracts of Papers, 17th Spring Symposium of the Pittsburg Catalysis Society, April, 1978.

U.S. Pat. No. 4,133,966 (Pretzer et al) relates to a process for selectively preparing ethanol from methanol, hydrogen and carbon monoxide in the presence of a catalytic system containing cobalt acetylacetonate, an iodine compound as a first promoter, a ruthenium compound as a second promoter and a tertiary organo Group VA compound. In order to avoid a wide variety of other products and optimize the formation of ethanol, patentees specify cobalt acetylacetonate as the cobalt source. If selectivity to acetaldehyde is desired, U.S. Pat. No. 4,151,208 (Pretzer et al) teaches a process wherein methanol, hydrogen and carbon monoxide are contacted with cobalt (II) meso-tetraaromaticporphine and an iodine promoter.

It would be desirable to have a single catalyst system which can efficiently convert methanol to acetaldehyde or ethanol with a high degree of selectivity and without the formation of substantial amounts of undesirable by-products.

SUMMARY OF THE INVENTION

In one aspect of the invention, it has been discovered that the selective conversion of methanol to acetaldehyde, ethanol or mixtures thereof can be accomplished by a catalytic system containing cobalt-ruthenium complexes or mixtures of specific cobalt compounds with ruthenium compounds. The present process for the homogeneous conversion of methanol to acetaldehyde, ethanol or mixtures thereof comprises contacting methanol with carbon monoxide and hydrogen in a $CO:H_2$ ratio of from 1:10 to 10:1 at a temperature of from about 100° to 300° C. and a pressure of from about 2 to 100 MPa in the presence of a catalytically effective amount of catalyst system, said catalyst system consisting essentially of (a) cobalt-ruthenium complexes selected from the group consisting of $HRuCo_3(CO)_{12}$, $M[RuCo_3(CO)_{12}]$, $C_5H_5Ru(P\phi_3)_2Co(CO)_4$, $HCoRu_3(CO)_{13}$ and $M[CoRu_3(CO)_{13}]$ wherein M is a cation, or a soluble ruthenium compound plus $Co_2(CO)_{8-n}(PR_3)_n$ where n is from 0 to 4 and each R is independently $C_1$ to $C_{20}$ aliphatic radical, $C_6$ to $C_{10}$ aryl, aralkyl having from 1 to 6 carbon atoms in the alkyl, $C_3$ to $C_8$ cycloalkyl; (b) iodine or an iodide promoter and (c) a phosphorus compound of the formula $PR_3$ or $P(OR)_3$, R being defined as above, with the proviso that if either the ruthenium or cobalt in component (a) bears a phosphorus-containing ligand, component (c) may be omitted.

The homogeneous catalytic system of the invention provides a highly selective method of producing ethanol or acetyldehyde by the homologation of methanol. The present process can achieve methanol conversions to ethanol of about 50 to 60% with only small amounts of by-products such as methyl ethyl ether, diethyl ether, propanol and ethyl acetate. The attainable selectivity to ethanol is about 80% and the total selectivity to acetaldehyde plus ethanol is about 93%. These are significantly higher selectivities compared to prior art processes, especially those producing ethanol or acetaldehyde using heterogeneous catalysts and the Fischer-Tropsch reaction.

DETAILED DESCRIPTION OF THE INVENTION

Figure 1:
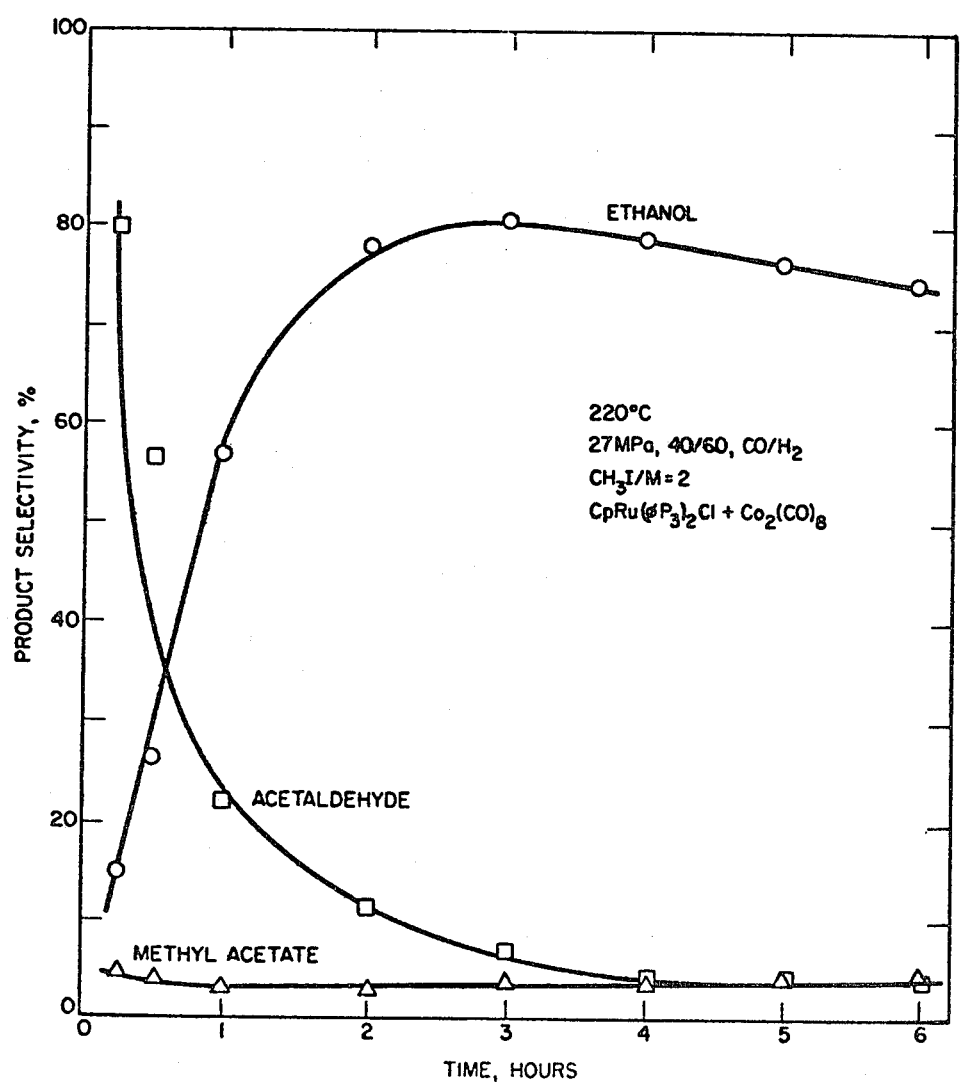
FIG. 1 is a graph showing ethanol selectivity as a function of reaction time.

With the exception of $HRuCo_3(CO)_{12}$, $MRuCo_3(CO)_{12}$, $HCoRu_3CO_{13}$ and $M[CoRu_3(CO)_{13}]$ where M is a cation such as alkali metal, $NR_1R_2R_3R_4^{\oplus}$, $PR_1R_2R_3R_4^{\oplus}$ or $\phi_2PNP\phi_2$ where $R_1$ to $R_4$ are independently hydrogen, $C_1$ to $C_{20}$ alkyl, $C_3$ to $C_8$ cycloalkyl, benzyl, phenyl or phenyl substituted by $C_1$ to $C_6$ alkyl, $C_1$ to $C_6$ alkoxy or halogen, almost no compounds containing cobalt and ruthenium are known. A novel compound containing a cyclopentadienide (Cp) ligand can be prepared by a displacement reaction between $CpRu(P\phi_3)_2Cl$ and $TlCo(CO)_4$ in tetrahydrofuran. This reaction is generally and specifically illustrated as follows:

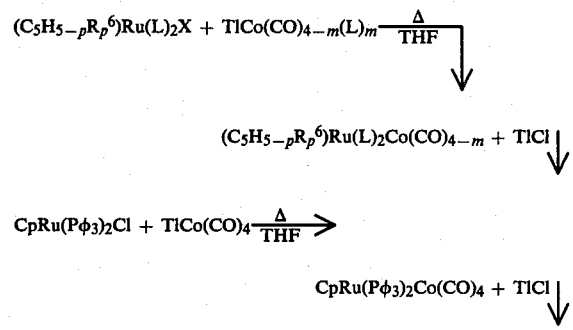

where $R^6$ is $C_1$ to $C_6$ alkyl, L is independently $PR_3$, CO or $P(OR)_3$ where R is defined above; X is halogen, p is a number from 0 to 5 and m is a number from 0 to 3.

As an alternative to employing a pre-formed cobalt-ruthenium complex, it is possible to use $Co_2CO_8$ or phosphine derivatives thereof plus a soluble ruthenium compound as a component in the catalyst system. The ratio of Co to Ru may range from 0.1:1 to 10:1. The preparation of $Co_2(CO)_8$ is well-known and compounds of the general formula $Co_2CO_{8-n}(PR_3)_n$ are prepared by ligand exchange reactions between $Co_2(CO)_8$ and $PR_3$. Suitable ruthenium compounds are those which are soluble in the reaction medium. Preferred ruthenium compounds include $CpRu(P\phi_3)_2Cl$, $Ru(acetylacetonate)_3$, $Ru(acetylacetonate)(CO)_2$, $Ru(CO)_3(P\phi_3)_2$ and $Ru_3(CO)_{12}$.

When $Co_2(CO)_8$ is dissolved in methanol, a rapid disproportionation takes place, i.e., $$12CH_3OH + 3Co_2(CO)_8 \rightarrow 2Co(CH_3OH)_6{}^{2+} + 4Co(CO)_4{}^- + 8CO.$$

Moreover, if the Ru compound contains a phosphine ligand such as $PR_3$ or $P(OR)_3$ or if such a phosphine ligand is added to a reaction mixture containing $Co_2(CO)_8$, it is likely that a ligand exchange reaction will occur. It is well-known that the thermal stability of cobalt complexes is enhanced by phosphine substitution (W. Hieber et al, *Chem. Ber.*, 94:1417 (1961)).

While not wishing to be bound by a theoretical or mechanistic discussion, it appears likely that the active catalytic species existing under reaction conditions are derivatives of the present cobalt-ruthenium complexes or mixtures of $Co_2(CO)_8$ or $Co_2(CO)_{8-n}(PR_3)_n$ plus Ru compound. This appears particularly likely in view of known Co and Ru ligand exchange reactions involving CO and $PR_3$. If this is correct, then the starting compounds function as catalyst precursors.

The concentration of total cobalt and ruthenium may range from $1 \times 10^{-5}$ to $1 \times 10^{-1}$M, preferably $1 \times 10^{-4}$ to $1 \times 10^{-2}$ M. Higher concentrations are technically feasible but provide no particular advantage.

The preferred temperature range is from 140° to 230° C., most preferably from 170° to 220° C. Generally, acetaldehyde formation is favored by a lower temperature range of from 140° to 200° C. whereas the preferred range for ethanol is from 200° to 225° C.

The preferred pressure is to 10 to 80 MPa, especially 15 to 60 MPa (1 MPa≅10 atm). Pressures higher than 100 MPa are possible but usually require special equipment which is economically disadvantageous. It is most preferred to operate at as high a pressure as is technically or economically feasible.

The homologation reaction is promoted by iodine or iodides. Suitable iodides promoters include HI, alkali metal iodide, $R_1R_2R_3R_4N^{\oplus}I^{\ominus}$ or $R_1R_2R_3R_4P^{\oplus}I^{\ominus}$ where $R_1$ to $R_4$ are defined as hereinbefore. Preferred promoters are HI or $CH_3I$. The amounts of iodide as measured by the I:M ratio, i.e., the number of moles of iodide to total gram atoms of metal present (Co+Ru), is from 0.2:1 to 100:1, preferably from 0.5:1 to 4:1.

The presence of phosphines in the reaction mixture is important in achieving high methanol conversions. Preferred phosphines have the formula $PR_3$ or $P(OR)_3$ where R is preferably alkyl of 1 to 10 carbon atoms, cycloalkyl of 5 to 7 carbon atoms, phenyl, tolyl or benzyl. The phosphine may be a ligand on either the cobalt or ruthenium metal atom or may be added separately to the reaction mixture.

The reaction times can vary from about 0.1 to 24 hours. If acetaldehyde is the desired product, reaction periods of from 0.5 to 3 hours are preferred, whereas the preferred reaction times for ethanol are from 3 to 10 hours.

The homologation reaction is conducted in a solvent. Since methanol is a reactant, it is the preferred solvent. While other organic solvents, which are inert under reaction conditions, may be employed, e.g., ethers and aromatics, they provide no advantage over methanol and require an additional separation step.

The reactor is pressurized with CO and $H_2$ at a $H_2$:CO ratio of from 10:1 to 1:10, preferably 5:1 to 1:5. If acetaldehyde is the desired product, then a $H_2$:CO range of from 0.5:1 to 1:1 is preferred. Excess hydrogen favors the formation of ethanol and the preferred $H_2$:CO ratio is from 1.3:1 to 3:1.

The process may be conducted in a batchwise or continuous manner in a conventional high pressure reactor having heating and agitation means. In general, the reactor is charged with methanol containing dissolved metal (Ru+Co) compound, flushed with CO and pressurized with the desired $CO/H_2$ mixture. The reactor is heated with agitation and the pressure adjusted using the $CO/H_2$ mixture. After the reaction is completed, the products are isolated using conventional techniques such as distillation.

While not wishing to limit the invention to any particular reaction mechanism, the above conditions with respect to reaction parameters may be explained as follows. The first product formed in the homologation of methanol is probably acetaldehyde, which is formed from the reduction of a catalytic intermediate into which CO has been inserted. Acetaldehyde can react with methanol to form an acetal but the acetal will react with water to regenerate acetaldehyde. Acetaldehyde is a reactive species and can be further reduced to ethanol. On the other hand, it is known that ethanol is much less reactive to homologation than is methanol.

Since the reduction of acetaldehyde is the more difficult reaction, it can be seen that if high selectivity to acetaldehyde is desired, one should use lower temperature, shorter reaction times and CO:$H_2$ ratios wherein excess $H_2$ is avoided. In contrast, if ethanol is the desired product, higher temperatures, longer reaction times and higher $H_2$:CO ratios to provide excess hydrogen are desirable so that acetaldehyde is reduced. Preferred conditions for acetaldehyde formation are temperatures of from 140° to 200° C., an $H_2$:CO ratio from about 0.5:1 to 1:1 and reaction times of from 1 to 3 hours, whereas preferred ethanol reaction conditions are temperatures of from 200° to 220° C., $H_2$:CO ratios of from 1.3 to 1 to 3:1 and reaction times of from 3 to 10 hours. The very high selectivities achievable for ethanol indicates that ethanol formation can be achieved without substantial by-product formation.

The process of the invention is further illustrated in the following examples.

EXAMPLES

Example 1

$HRuCo_3(C)_{12}$ and its salts are prepared according to methods described in *J. Chem. Soc.* (A):1444 (1968). $PPNCoRu_3(CO)_{13}$ was prepared by the reaction of $PPNCo(CO)_4$ and $Ru_3(CO)_{12}$ (PPN=$\phi_2$PNP$\phi_2$).

The preparation of $CpRu(P\phi_3)_2Co(CO)_4$ is described as follows. $TlCo(CO)_4$ and $CpRu(P\phi_3)_2Cl$ were prepared by known methods (*J. Organomet. Chem.*, 43:C44 (1972); *Aust. J. Chem.*, 30:1601 (1977)). A mixture of 1.88 g (5 mmoles) $TlCo(CO)_4$ and 3.63 g (5 mmoles) $CpRu(P\phi_3)_2Cl$ in 75 ml THF was refluxed for 18 hours under nitrogen. The cooled solution was filtered to remove the TlCl which precipitated (1.16 g) and the deep colored filtrate was added to 200 ml pentane and the solution chilled to −20° C. overnight. The deep purple crystals which formed were collected on a filter and dried under nitrogen. Yield 1.2 g (28%).

Analysis. Calculated for $C_{45}H_{30}P_2O_4CoRu$, C, 62.74; H, 4.10; P, 7.19; Co, 6.84; Ru, 11.73. Found: C, 62.79; H, 4.30; P, 6.98; Co, 6.55; Ru, 11.44.

Example 2

The homologation of methanol to ethanol is described in this example. The reaction parameters are 0.86 g of the complex of Example 1, reaction temperature=220° C.; $H_2$:CO=1.5; pressure=27 MPa; $CH_3I$:metal=2; methanol:metal=4400 and residence time=6 hours. The reaction was carried out as follows.

The high pressure reaction (27 MPa) was carried out in an Autoclave Engineers 1 liter stirred autoclave which was equipped with a catalyst blowcase and which was directly fed by high pressure syn-gas lines. The autoclave was charged with 250 ml methanol with 50 ml toluene as an internal standard and the appropriate amount of methyl iodide, and preheated to the reaction temperature. The catalyst dissolved in 100 ml methanol was then introduced through the blowcase and the pressure immediately brought to the desired level. Liquid samples were taken at desired intervals during the reaction and a gas sample was taken at the conclusion of the reaction.

Gas and liquid products were analyzed by gas chromatography using a Perkin-Elmer model 900 or Hewlett Packard Model 5840A instrument. Columns packed with Chromosorb 102 or Carbowax 20M on Gas Chrom Q were used with temperature programming. Peaks were identified by comparison of known compounds on two different columns if possible. For peaks which could not be identified in this manner, identification was made by gas-chromatograph-mass spectroscopy.

Quantitative measures were made using toluene as an internal standard. Response factors were either determined experimentally or were taken from the compilation of Dietz (*J. Gas Chrom.*, 5:68 (1967)).

The results are summarized in Table 1.

TABLE I

PRODUCT DISTRIBUTION FROM METHANOL HOMOLOGATION

| Product | Approximate Percentage of Methanol Converted* Co—Ru |
|---|---|
| Methane | 1 |
| Dimethylether | 2 |
| Methylethylether | 3 |
| Acetaldehyde | Trace |
| Ethanol | 80 |
| Methyl Acetate | 2 |
| Diethyl Ether | 3 |
| n-propanol | 5 |
| Ethyl Acetate | 3 |

*Methanol conversion = 54%.

As can be seen from the data, high selectivities to ethanol can be achieved using a ruthenium-cobalt complex.

Example 3

This example is directed to a comparison of Co complexes, Ru complexes and mixtures thereof versus the preformed Ru-Co complex with respect to the homologation reaction. Example 2 was repeated except that the active metal of the catalyst system was varied. Table II summarizes the results.

TABLE II

METHANOL HOMOLOGATION WITH Co—Ru CATALYSTS

| Catalyst | Methanol Conversion | Ethanol Selectivity |
|---|---|---|
| $CpRu(P\phi_3)_2Co(CO)_4$ | 54 | 80 |
| $Co_2(CO)_8$ | 10 | 30 |
| $CpRu(P\phi_3)_2Cl$ | 9 | 60 |
| $Co_2(CO)_8 + P\phi_3$ | 29 | 30 |
| $CpRu(P\phi_3)_2Cl + Co_2(CO)_8$ | 58 | 86 |

Six-hour residence time, 220° C., 27 MPa, 40/60 $CO/H_2$, $CH_3I$/metal ratio=2, methanol/metal ratio=4400.

These data show that either $CpRu(P\phi_3)_2Co(CO)_4$ or mixtures of $CpRu(P\phi_3)_2Cl$ plus $Co_2(CO)_8$ provide about the same methanol conversions and ethanol product selectivities. Both the preformed complex and the above-cited mixture have a substantial advantage over the individual metal components. The Co and Ru complex mixture is unexpectedly superior as compared to the expected additive effects of the individual metal complexes.

FIG. 1 illustrates product selectivity as a function of reaction time. The figure indicates that at 220° C., maximum selectivity to ethanol occurs at from about 3 to 6 hours.

Example 4

The effect of temperature, phosphine ligand and metal is illustrated in this example. The procedure of Example 2 was followed except that the residence time was 3 hours and the nature of the metal component of the catalyst system was varied. The data are shown in Table III.

TABLE III

METHANOL HOMOLOGATION CATALYZED BY Co—Ru AND Ru—Rh MIXTURES

| Example No. | Catalyst | Temp. | Methanol Conversion | Product Selectivity Ethanol | Product Selectivity Acetaldehyde |
|---|---|---|---|---|---|
| A. | $CpRu(\phi_3P)_2Cl + Co_2(CO)_8$ | 220° | 41 | 88 | 5 |
| B. | $CpRu(\phi_3P)_2Cl + Co_2(CO)_8$ | 180° | 33 | 10 | 77 |
| C. | $Ru(acac)_3* + Co_2(CO)_8$ | 220° | 7 | 68 | — |
| D. | $Ru(acac)_3$ | 220° | trace | | |
| E. | $Rh(acac)(CO)_2$ | 180° | trace | | |
| F. | $Rh(acac)(CO)_2 + CpRu(\phi_3P)_2Cl$ | 180° | trace | | |

*acac = acetylacetone.
Three-hours residence time, 27 MPa; 40/60 $CO/H_2$; $CH_3I$/metal ratio = 4; methanol/metal ratio = 4440.

By comparing Examples A and B in Table III, it is seen that lower temperatures favor acetaldehyde formation over ethanol. A reduction of the $CO:H_2$ ratio to 1:1 would further increase the selectivity to acetaldehyde. The importance of the phosphine ligand is demonstrated by comparing Examples A and C. Only a 7% methanol conversion is achieved when $Ru(acac)_3$ is substituted for $CpRu(P\phi_3)_2Cl$. Finally, the substitution of Rh for Co produces a catalyst system which is virtually inactive for methanol homologation (Examples A and F) under these conditions.

Example 5

According to U.S. Pat. No. 4,133,966, paragraph bridging columes 4 and 5, most cobalt sources for the production of ethanol from methanol, carbon monoxide, and hydrogen have the disadvantage of producing a variety of alcohols and their derivatives, and do not optimize the formation of ethanol. In contrast, the cobalt-containing catalyst system of the present invention achieves comparable or better selectivities to those shown in U.S. Pat. No. 4,133,966. Under present conditions and catalyst systems where ethanol selectivity is low, acetaldehyde selectivity is high, and no change in the catalyst system is required as is indicated by comparing U.S. Pat. Nos. 4,133,966 and 4,151,208. These results and comparisons are set forth below.

The reaction parameters and procedures disclosed in Examples I–VII and summarized in Table I of U.S. Pat. No. 4,133,966 were followed. After quenching the reaction by external cooling, the reaction mixture was analyzed as described in Example 2 herein. The data are summarized in Table IV.

TABLE IV

| Ex. No. | Catalyst System | Co/Ru Molar Ratio | % Methanol Conversion 3hr. | 6hr. | % Ethanol Selectivity 3hr. | 6hr. | % Acetaldehyde Selectivity 3hr. | 6hr. | Temp °C. |
|---|---|---|---|---|---|---|---|---|---|
| A. | $Co(acac)_2$, $Ru(acac)_3$, $P\phi_3$, $I_2$ | 3:0.75 3:0.75 | 44 68 | 62 80 | 54 60 | 58 48 | 1 1 | <1 <1 | 175 220*** |
| B. | $Co_2(CO)_8$ $Ru(acac)_3$, $P\phi_3$, $I_2$ | 3:0.75 | 47 60 | 64 77 | 55 73 | 56 53 | 3 1 | 2 <1 | 175 220*** |
| C. | $Co_2(CO)_8$, $CpRu(P\phi_3)_2Cl$, $I_2$ | 3:0.75 | 45 80 | 67 97 | 19 58 | 24** 48 | 33 4 | 18 <1 | 175 220*** |
| D. | $Co_2(CO)_6(P\phi_3)_2$* $Ru(acac)_3$, $I_2$ | 3:0.75 | 23 | 42 | 67 | 68 | 6 | 2 | 175 |
| E. | $CpRu(P\phi_3)_2Co(CO)_4$, $I_2$ | 3:0.75 | 41 | 62 | 02 | 08** | 51 | 33 | 175 |

Cobalt: iodine molar ratio = 2:1
Cobalt: $\phi_3P$ molar ratio = 6:1
Pressure = 4000 psig
$CO:H_2$ = 1:1
*Solubility problems limited catalyst concentration to ½ that of other examples.
**Major product = acetaldehyde
***$CH_3I$ substituted for $I_2$ at higher temperature, no improvement in methanol conversion noted for $I_2$.

A comparison of the results of Table IV with Example VI in U.S. Pat. No. 4,133,966 shows that other cobalt sources can achieve ethanol selectivities comparable to or better than cobalt acetylacetonate. In Experiments C. and E. of Table IV, selectivities to ethanol were low, but acetaldehyde selectivities were correspondingly high, and an increase in temperature to 200° C. would favor ethanol formation with these particular catalysts. It is noted that under more favorable experimental conditions, the catalyst system of the present invention can achieve ethanol selectivities of about 80-90% (of Tables I and II herein).

In order to achieve improved conversions at elevated temperatures (220° C.), $CH_3I$ was substituted for $I_2$ as a promoter. When $I_2$ is used at the higher temperatures, no significant improvement in conversion occurs and $CH_4$ becomes a significant impurity forming in amounts of about 5–10% based on the reacted methanol. At 175° C. under the experimental conditions for Table IV, $CH_3I$ increases methanol conversion but also results in increased acetaldehyde formation and decreased ethanol formation.

What is claimed is:

1. A process for the homogeneous conversion of methanol to acetaldehyde, ethanol or mixtures thereof which comprises contacting methanol with carbon monoxide and hydrogen in a $CO:H_2$ ratio of from 10:1 to 1:10 at a temperature of from about 100° to 300° C. and a pressure of from about 2 to 100 MPa in the presence of a catalytically effective amount of a catalyst system, said catalyst system consisting essentially of:
   (a) cobalt-ruthenium complexes selected from the group consisting of $HRuCo_3(CO)_{12}$, $M[RuCo_3(CO)_{12}]$, $HCoRu_3(CO)_{13}$, $M[CoRu_3(CO)_{13}]$ and $C_5H_5Ru(P\phi_3)_2Co(CO)_4$ where M is a cation;
   (b) an iodine or iodide promoter; and
   (c) a phosphorus compound of the formula $PR_3$ or $P(OR)_3$ where R is independently a $C_1$ to $C_{20}$ aliphatic radical, $C_6$ to $C_{10}$ aryl, aralkyl having from 1 to 6 carbon atoms in the alkyl or $C_3$ to $C_8$ cycloalkyl, with the proviso that if either the ruthenium or cobalt in component (a) bears a $PR_3$ or $P(OR)_3$ ligand, component (c) may be omitted.

2. The process of claim 1 wherein component (a) is $C_5H_5Ru(P\phi_3)_2Cl$ plus $Co_2(CO)_8$.

3. The process of claim 1 wherein component (a) is $C_5H_5Ru(P\phi_3)_2Co(CO)_4$.

4. The process of claim 1 wherein the concentration of component (a) is from 0.00001 M to 0.1 M.

5. The process of claim 1 wherein the temperature is from 140° to 230° C.

6. The process of claim 1 wherein the pressure is from 15 to 60 MPa.

7. The process of claim 1 wherein component (b) is at least one of hydrogen iodide, methyl iodide, tetraalkyl ammonium iodide or tetraphenyl phosphonium iodide.

8. The process of claim 1 wherein the ratio of iodide to total gram atoms of cobalt plus ruthenium is from 0.5:1 to 100:1.

9. A process for the homogeneous conversion of methanol to acetaldehyde, ethanol or mixtures thereof which comprises contacting methanol with carbon monoxide and hydrogen in a $CO:H_2$ ratio of from 10:1 to 1:10 at a temperature of from about 100° to 300° C. and a pressure of from about 2 to 100 MPa in the presence of a catalytically effective amount of a catalyst system, said catalyst system consisting essentially of:
   (a) cobalt-ruthenium complexes selected from the group consisting of $HRuCo_3(CO)_{12}$, $M[RuCo_3(CO)_{12}]$, $HCoRu_3(CO)_{13}$, $M[CoRu_3(CO)_{13}]$ and $C_5H_5Ru(P\phi_3)_2Co(CO)_4$ where M is a cation selected from the group consisting of alkali metal, $NR_1R_2R_3R_4^{\oplus}$, $PR_1R_2R_3R_4^{\oplus}$ and $\phi_2PNP\phi_2$ where $R_1$ to $R_4$ are independently hydrogen $C_1$ to $C_{20}$ alkyl, $C_3$ to $C_8$ cycloalkyl, benzyl, phenyl or phenyl substituted by $C_1$ to $C_6$ alkyl, $C_1$-$C_6$ alkoxy or halogen;
   (b) an iodine or iodide promoter; and
   (c) a phosphorus compound of the formula $PR_3$ or $P(OR)_3$ where R is independently a $C_1$ to $C_{20}$ aliphatic radical, $C_6$ to $C_{10}$ aryl, aralkyl having from 1 to 6 carbon atoms in the alkyl, $C_3$ to $C_8$ cycloalkyl, with the proviso that if the ruthenium in component (a) bears a $PR_3$ or $P(OR)_3$ ligand, component (c) may be omitted.

10. A process for the homogeneous conversion of methanol to acetaldehyde, ethanol or mixtures thereof which comprises contacting methanol with carbon monoxide and hydrogen in a $CO:H_2$ ratio of from 10:1 to 1:10 at a temperature of from about 100° to 300° C. and a pressure of from about 2 to 100 MPa in the presence of a catalytically effective amount of a catalyst system, said catalyst system consisting essentially of:
  (a) a soluble ruthenium compound selected from the group consisting of $(C_5H_5)Ru(P\phi_3)_2Cl$, $Ru(acetylacetonate)_3$, $Ru(acetylacetonate)(CO)_2$, $Ru(CO)_3(P\phi_3)_2$ and $Ru_3(CO)_{12}$ plus $Co_2CO_8$;
  (b) an iodine or iodide promoter; and
  (c) a phosphorus compound of the formula $PR_3$ or $P(OR)_3$ where R is independently a $C_1$ to $C_{20}$ aliphatic radical, $C_6$ to $C_{10}$ aryl, aralkyl having from 1 to 6 carbon atoms in the alkyl, $C_3$ to $C_8$ cycloalkyl, with the proviso that if the ruthenium in component (a) bears a $PR_3$ or $P(OR)_3$ ligand, component (c) may be omitted.

11. A process for the homogeneous conversion of methanol to acetaldehyde, ethanol or mixtures thereof which comprises contacting methanol with carbon monoxide and hydrogen in a $CO:H_2$ ratio of from 10:1 to 1:10 at a temperature of from about 100° to 300° C. and a pressure of from about 2 to 100 MPa in the presence of a catalytically effective amount of a catalyst system, said catalyst system consisting essentially of:
  (a) $(C_5H_{5-p}R^6{}_p)Ru(L)_2Co(CO)_{4-m}$ where $R^6$ is $C_1$–$C_6$ alkyl, L is $PR_3$, CO or $P(OR)_3$ where each R is independently $C_1$–$C_{20}$ aliphatic radical, $C_6$–$C_{10}$ aryl, aralkyl having from 1 to 6 carbon atoms in the alkyl or $C_3$–$C_8$ cycloalkyl, p is a number from 0 to 5 and m is a number from 0 to 3;
  (b) an iodine or iodide promoter; and
  (c) a phosphorus compound of the formula $PR_3$ or $P(OR)_3$, R being defined above, with the proviso that if the ruthenium in component (a) bears a $PR_3$ or $P(OR)_3$ ligand, component (c) may be omitted.

12. The process of claim 11 wherein component (a) is $(C_5H_5)Ru(P\phi_3)_2Co(CO)_4$.

13. A process for the homogeneous conversion of methanol to acetaldehyde, ethanol or mixtures thereof which comprises contacting methanol with carbon monoxide and hydrogen in a $CO:H_2$ ratio of from 10:1 to 1:10 at a temperature of from about 100° to 300° C. and a pressure of from about 2 to 100 MPa in the presence of a catalytically effective amount of a catalyst system, said catalyst system consisting essentially of:
  (a) $C_5H_5Ru(P\phi_3)_2Cl$ plus $Co_2(CO)_8$; and
  (b) an iodine or iodide promoter.

14. A process for the homogeneous conversion of methanol to acetaldehyde, ethanol or mixtures thereof which comprises contacting methanol with carbon monoxide and hydrogen in a $CO:H_2$ ratio of from 10:1 to 1:10 at a temperature of from about 100° to 300° C. and a pressure of from about 2 to 100 MPa in the presence of a catalytically effective amount of a catalyst system, said catalyst system consisting essentially of:
  (a) $C_5H_5Ru(P\phi_3)_2Co(CO)_4$; and
  (b) an iodine or iodide promoter.

15. The process of claims 11 or 14 wherein the temperature is from 140° to 230° C.

16. The process of claims 10 or 13 wherein the temperature is from 140° to 230° C.

* * * * *